United States Patent [19]

Woodward et al.

[11] Patent Number: 4,597,975

[45] Date of Patent: Jul. 1, 1986

[54] IODINE SURFACE ACTIVE COMPOSITIONS

[76] Inventors: Fred E. Woodward, 200 Churchill Rd., W. Palm Beach, Fla. 33405; Alice P. Hudson, 728 W. Kalmia Dr., Lake Park, Fla. 33403

[21] Appl. No.: 540,372

[22] Filed: Oct. 11, 1983

Related U.S. Application Data

[63] Continuation-in-part of Ser. No. 319,075, Nov. 6, 1981, abandoned, which is a continuation-in-part of Ser. No. 160,374, Jun. 17, 1980, abandoned, which is a continuation of Ser. No. 829,520, Aug. 31, 1977, abandoned, which is a continuation-in-part of Ser. No. 722,493, Sep. 13, 1976, abandoned, which is a continuation-in-part of Ser. No. 577,274, May 14, 1975, abandoned, and Ser. No. 577,303, May 14, 1975, abandoned.

[51] Int. Cl.$^4$ .................. A01N 59/12; A01N 33/24
[52] U.S. Cl. ................................. 424/150; 514/644
[58] Field of Search .................. 424/150; 514/644

[56] References Cited

U.S. PATENT DOCUMENTS

| | | | |
|---|---|---|---|
| 2,977,315 | 3/1961 | Scheib et al. | 252/106 |
| 3,028,299 | 4/1962 | Winicov et al. | 424/150 |
| 3,380,923 | 4/1968 | Beach | 252/106 |
| 3,484,523 | 12/1969 | Findlan et al. | 424/248 |
| 3,534,102 | 10/1970 | Waldstein | 260/584 |
| 3,808,311 | 4/1974 | Olson et al. | 424/70 |
| 3,821,124 | 6/1974 | Dixon | 424/150 X |
| 4,206,204 | 6/1980 | Langford | 424/150 |
| 4,207,310 | 6/1980 | Langford | 424/150 |

OTHER PUBLICATIONS

Kirk-Othmer—"Encyclopedia of Chemical Technology", 2nd ed., Supplemental vol., 1971, pp. 32-36, 43-46.

*Primary Examiner*—Leonard Schenkman

[57] ABSTRACT

Iodine-containing surface active compositions, useful for cleansing and degerming skin, possessing high lather, good emolliency, mildness, and a pleasant afterfeel; and also iodine-containing compositions useful for cleaning and degerming hard surfaces, possessing good detergency and long lasting biocidal activity, contain certain surface active amine oxides and iodine in the form of an amine oxide-triiodide undissociated salt.

18 Claims, No Drawings

IODINE SURFACE ACTIVE COMPOSITIONS

CROSS REFERENCE TO RELATED APPLICATIONS

This application is a continuation in part of Ser. No. 319,075 filed Nov. 6, 1981, now abandoned, which was a continuation in part of Ser. No. 160,374, filed June 17 1980, now abandoned, which was a continuation of Ser. No. 829,520, filed Aug. 31, 1977, now abandoned, which was a continuation-in-part of Ser. No. 722,493, filed Sept. 13, 1976, now abandoned, which was a continuation-in-part of Ser. No. 577,274 and 577,303, filed May 14, 1975, also abandoned.

BACKGROUND OF THE INVENTION

1. Field of the invention

This invention relates to iodine-containing surface active compositions, useful for cleansing and degerming skin, possessing cosmetically appealing properties such as high lather, good emolliency, mildness, and a pleasant afterfeel, and also to iodine-containing compositions useful for cleaning and degerming hard surfaces, possessing good detergency and long-lasting biocidal activity.

Iodine-containing preparations are known to be excellent germicides in that they will kill rapidly a broad spectrum of bacteria and viruses. However, previously known surfactant or polymeric complexing agents for iodine must be formulated with additional surfactants to make products suitable for hand washing or more general human cleansing problems, because they lack cosmetic appeal in that they are not superior lathering and foaming compositions, they lack emolliency, and in most cases are irritating to skin. An object of our invention is an iodophor that possesses good lather, emolliency, and mildness in and of itself.

It is not possible with previously known iodophors to formulate products with low levels of iodine for use without dilution in products such as douches, because at low levels of both iodine and complexing agent the iodine has a high vapor pressure, and if more complexing agent is added the iodine is unstable. It is a further object of this invention to provide formulations with low iodine vapor pressure and stable iodine at very low levels of iodophor so that they will have the cosmetic appeal of less intense colors, and a broader range of useful concentrations.

Previously known iodophors have limited shelf life because the iodine continues to react, however slowly, regardless of the age of the product. Another object of this invention is a product with a greatly extended shelf life because an equilibrium level of iodine is reached which does not change on storage.

Iodophors used as hard surface detergents usually contain ethoxylated surfactants as the iodine carrier. When these detergents are diluted to 25 to 50 ppm iodine, the iodine is no longer associated with the ethoxylated surfactant and reacts rapidly with any organic matter present and is destroyed. It is a further object of this invention to provide formulations in which the iodine remains associated with the surfactant at high dilutions so that the stability of the iodine in the presence of organic matter is improved while the biocidal activity remains high.

2. Description of the prior art

Iodophors suitable for use as biocidal cleaners of hard surfaces are well known articles of commerce. They are iodine "complexes" made from nonionic surfactants of the type

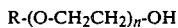

where $n \times 44$ = approximately 60 percent or more of the molecular weight of the surfactant molecule, or

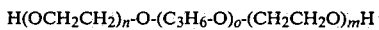

where $(m+n) \times 44 = 20$ percent or more of the molecular weight of the surfactant molecule. Many such examples occur, for instance in U.S. Pat. Nos. 3,028,299 and 2,971,777. However, nonionic surfactants of the above type of themselves are not suitable for hand washing products because they do not lather and lack emolliency. When diluted for use as hard surface cleaners the iodine vapor pressure is greatly increased, making the iodine in the diluted solutions unstable.

Ethoxylated amines and quaternized ethoxylated amines (U.S. Pat. Nos. 3,028,299 and 3,539,520) have been used both by themselves and in combination with nonionic surfactants to complex iodine. These amines and quaternaries contain at least 15 ethyleneoxy groups so that the condensed ethylene oxide represents a substantial portion of the molecule, and thus have the poor cosmetic properties of the nonionic surfactants. Iodophors of quaternary ammonium salts that do not contain condensed ethylene oxide are disclosed in U.S. Pat. No. 2,679,533. These iodophors tend to precipitate and are not suitable for extended storage.

Polyvinylpyrrolidone is used to make iodophor powder concentrates (U.S. Pat. Nos. 2,706,701; 2,900,305; and 3,028,300). They require the addition of lathering and/or detergent surfactants to make products for topical or hard surface cleaning. Nor can they be diluted extensively without an unacceptable rise in iodine vapor pressure.

Acid is traditionally added to iodophors (U.S. Pat. Nos. 3,029,183; 3,308,014; 2,977,315; and 3,274,116). Iodine is most biocidal at pH values below 4 so sufficient acid is added to reduce the pH to this value in the product as used. Beyond this acid may be added to assist cleaning (as in removing milkstone in dairy equipment). Organic acids such as hydroxyacetic acid can help solubilize the iodophor in some instances.

Iodophors have been prepared from equimolar mixtures of ethoxylated amine oxides and iodine (U.S. Pat. No. 3,534,102). Ethoxylated amine oxides with about 15 moles of condensed ethylene oxide or more are similar to nonionic surfactants in that they do not lather and lack emolliency. Amine oxides with only two moles of condensed ethylene oxide, when reacted with a molar equivalent of iodine are water insoluble. Without any added acid the products lack shelf stability.

Columns or beds of strongly basic anion exchange resins containing combined triiodide have been used to disinfect water (U.S. Pat. Nos. 3,817,860 and 3,923,665). Such compositions are not suitable for liquid cleaning products in that they are insoluble beads.

Amphoteric surfactants containing amine or quaternary ammonium groups, and sulfate or carboxylate groups have been used to prepare iodophors (U.S. Pat. No. 3,380,923). Such products tend to precipitate unless either a substantial amount of nonionic surfactant is present or the amphoteric surfactant itself contains condensed ethylene oxide. They also have high iodine vapor pressure on dilution.

Amine oxides are commonly used in shampoos and other detergent products (U.S. Pat. Nos. 3,808,311; 4,133,779; 4,065,409; 3,959,157 and numerous others). They are known to be mild to skin and possess good detergency. They are usually used at pH values above about 5 so that they are compatable with anionic detergents.

SUMMARY OF THE INVENTION

The present invention is based in part on the discovery that surface active amine oxides of the type herein described can be reacted with iodine and a suitable acid to form undissociated and insoluble but highly biocidal salts with the triiodide ion. This salt can be solubilized by the use of an excess of the amine oxide alone, by a mixture of excess amine oxide and other surfactants herein described, or by other surfactants alone. This makes possible the incorporation of the highly desirable germicidal triiodide salt in a mild, lathering, cosmetically appealing form not heretofore attainable. It was also discovered that strict limits were necessary on the amount and type of acid used with the amine oxides to obtain the amine oxide-triodide salt.

In a surprising adjunct of the invention, it is shown that the amine oxide-triiodide salt forms even when the iodophor is made in the presence of nonionic (polyethyleneoxy-containing) surfactants or polyvinylpyrrolidone; that it is more effective in degerming than are presently known iodophors; and that there is no free molecular iodine ($I_2$) present, and thus no iodine vapor pressure at any dilution.

DETAILED DESCRIPTION OF THE INVENTION

This invention relates to compositions for cleansing and degerming skin and compositions for cleansing and degerming hard surfaces, which compositions contain (a) a protonated amine oxide-triiodide salt of the structure

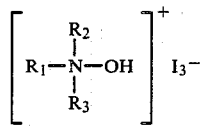

(b) a protonated amine oxide salt of the structure

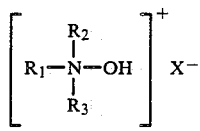

(c) an amine oxide of the structure

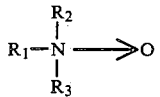

(d) a water soluble acid of the structure HY, and (e) one or more substances chosen from the group consisting of (1) surface active phosphate esters (2) nonionic surfactants (3) water soluble solvent alcohols, wherein $R_1$ is alkyl, acylamidopropyl, alkoxy propyl and mixtures thereof, each said alkyl and acyl group containing about 10 to 18 carbon atoms and no unsaturation; $R_2+R_3$ are lower alkyl which taken together contain no more than 6 carbon atoms and are preferrably methyl; Y is a radical selected from the group consisting of phosphate, phosphate ester, chloride, bromide, lactate, citrate, malate, glycolate, formate, oxalate, tartrate, and sulfate; and X is a radical selected from the group consisting of iodide and Y; the molar ratio of (a) to (b)+(c) being less than about 0.5 to 1 and preferrably between 0.5 to 1 and 0.01 to 1, the molar ratio of (b) to (c) being at least about 2 to 1, (d) being present at a level sufficient to effect a pH of about 4.3 or lower and preferably between 4.3 and 0.2; and (b)+(c) or said group substance (e), or (b)+(c) and said group substance (e) taken together being present in an amount at least sufficient to effect a transparent solution, (b)+(c) being preferred; and said solution containing no molecular iodine as determined spectrophotometrically.

Also included in the invention are compositions comprising (a) a protonated amine oxide-trihalide salt of the structure

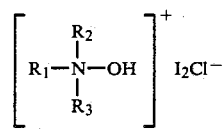

(b) a protonated amine oxide salt of the structure

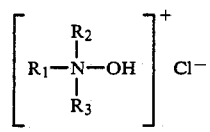

(c) hydrochloric acid wherein $R_1$, $R_2$, and $R_3$ are as described above, the molar ratio of (a) to (b) being between about 0.20 to 1 and 0.01 to 1, and the molar ratio of (c) to (a)+(b) being at least about 1 to 1.

These compositions result from chemical reactions which occur on mixing amine oxides, iodine and acids herein described.

The amine oxides used according to our invention are of the general formula

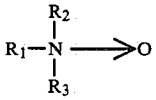

in which $R_1$ is $C_{10}$ to $C_{18}$ alkyl and mixtures thereof, alkyl oxypropyl or acyl amidopropyl, said alkyls containing 10 to 18 carbon atoms, and mixtures thereof, and $R_2$ and $R_3$ are lower alkyl, and taken together have no more than 6 carbon atoms. The preferred amine oxides are straight chain alkyldimethyl amine oxides in which the alkyl amine is made by the following series of reactions where R is a mixture of $C_{10}$ and $C_{12}$ hydrocarbon.

R-CH$_2$CH$_2$Br+2(CH$_3$)$_2$NH→R-CH$_2$CH$_2$N(CH$_3$)$_2$+(CH$_3$)$_2$NH$_2$Br

The HBr and excess dimethylamine are recovered. The amines are converted to amine oxides by the method described in U.S. Pat. No. 2,169,976, and if necessary are further purified by treatment with an excess of hydrogen peroxide to assure complete freedom from alkyldimethylamine.

Amine oxides made from fatty amines produced from natural sources such as coconut oil or tallow are in general unsatisfactory, as they invariably contain unsaturation and other unspecified impurities which react with iodine. The alkylation of such fatty amines with methyl chloride or formaldehyde and formic acid also gives rise to impurities.

Also unsatisfactory are amine oxides made from tertiary amine resulting from the addition of two moles of ethylene oxide to one mole of fatty amine. These products tend to have poor lathering characteristics and somewhat poorer iodine stability.

Other amine oxides which fall within the scope of our invention and which may even be preferred for reasons of solubility or lathering properties include that group of amine oxides in which R$_1$ is interrupted by ether or amide groups. For example, alkyloxypropylamines from the reaction of alkyl alcohols with acrylonitrile and subsequent reduction to the amine are methylated by standard procedures such as with formic acid and formaldehyde and then converted to alkyloxypropyl-dimethylamine oxides. The amine oxides of acyl amides of dimethylaminopropylamine are made and sold.

Amine oxides as described above in which R$_1$ contains 14 carbon atoms or less have excellent lathering properties, while those in which R$_1$ contains 14 carbon atoms or more have emollient properties. Thus by the judicious combining of lathering and emollient amine oxides, formulas with excellent lather and emolliency can be obtained.

We have discovered that amine oxides as described above will react with iodine and acid in water solution to form the insoluble protonated amine oxide-triiodide salt (a) and the protonated amine oxide salts (b). The following reactions are suggested by our experimental results.

The initial reaction between amine oxides and iodine is the formation of a molecular or "charge transfer" complex:

$$R_3N \rightarrow O + I_2 \rightarrow R_3N - OI_2 \quad (1)$$

which ionizes:

$$R_3N - OI_2 \rightarrow R_3NOI^+ + I^- \quad (2)$$

and reacts with water:

$$R_3NOI^+ + H_2O \rightarrow R_3NOH^+I^- + H^+ + \tfrac{1}{2}O_2 \quad (3)$$

These reactions are rapid and intermediate species are not present in the resulting compositions. When additional iodine is present species (a) forms:

$$R_3NOH^+I^- + I_2 \rightarrow R_3NOH^+I_3^- \quad (4)$$

This protonated amine oxide triiodide salt does not dissociate in water and is by itself insoluble. It is much more stable in the presence of organic matter than is molecular iodine, yet is highly biocidal.

Species (b) is formed in reaction (3) as well as from the reaction of amine oxide and added acid:

$$R_3N \rightarrow O + HY \rightarrow R_3NOH^+Y^- \quad (5)$$

Unreacted, neutral amine oxide is designated species (c). The protonated amine oxide salt (b) and neutral amine oxide (c) solublize the insoluble triiodide salt (a). The formation of species (b) also limits the amount of iodine which reacts by reactions (1), (2), and (3), since the initial reaction (1) cannot occur with the protonated species (b).

To form useful compositions the molar ratios at which the components are mixed must be chosen precisely. If insufficient acid is added, all of the iodine added will be reduced by reactions (1), (2), and (3) and no species (a) will be formed by reaction (4). If too much iodine is added only species (a) will form, resulting in a nonutile insoluble precipitate. Thus to prepare useful compositions we have found that the molar ratio of (a) to (b)+(c) must be about 0.5 to 1 or lower, and preferrably between 0.5 to 1 and 0.01 to 1. It can be seen that this results when from 2 to 67 moles of amine oxide per mole of iodine are used. The ratio of (b) to (c) must be at least about 2 to 1 and more preferrably at least 10 to 1, and most preferrably at least 20 to 1.

The acids employed in this invention must possess a pK$_a$ at least as low as the numerical value of the desired pH. A further restriction is that the acid may not contain isolated double bonds or other groups that are oxidizable by iodine. Table 1 lists a number of suitable acids and the values of their pK$_a$'s. Other suitable acids will be obvious to those skilled in the art.

TABLE 1

| Acid | pK$_a$ |
|---|---|
| phosphoric acid and phosphate esters | 2.12 |
| hydrochloric acid | 0 |
| hydrobromic acid | 0 |
| sulfuric acid | 0 |
| citric acid | 3.08 |
| formic acid | 3.75 |
| glycolic acid | 3.83 |
| malic acid | 3.40 |
| oxalic acid | 1.23 |
| phthalic acid | 2.89 |
| tartaric acid | 2.98 |

If the products are to be used on the skin, the quantity of acid added must be such that the pH is above 2.4 to prevent irritation. Preferred acids are phosphoric acid, and phosphate esters, citric acid, and malic acid. For hard surface detergents skin irritation is not as important, and the pH can be as low as 0.2. Preferred acids for hard surface detergents are phosphoric acid and hydrochloric acid. Less preferred acids are citric acid and glycolic acid.

Since the pK$_a$'s of the amine oxides of this invention are about 4.9, the acid must be sufficiently strong, and present in sufficient amount, to reduce the pH to about 4.3 or lower. The amine oxides at this pH is substantially (76 percent) protonated, or exists in the cationic form $$\left[ \begin{array}{c} R_2 \\ | \\ R_1-N-OH \\ | \\ R_3 \end{array} \right]^+ + X^-$$

This species maintains the equilibrium between $I^-$, $I_3^-$, and water in a useful range. A high degree of protonation encourages the formation of the desired triiodide ion. Table 2 shows the relationship between the pH of the solution and the extent to which the amine oxides are protonated.

TABLE 2

| pH | $HAO^+/AO$ | % protonated form |
|---|---|---|
| 2.4 | 316 | 99.7 |
| 2.9 | 100 | 99.0 |
| 3.4 | 31.6 | 96.9 |
| 3.9 | 10 | 90.9 |
| 4.4 | 3.2 | 76.0 |
| 4.9 | 1 | 50.0 |

If the ratio of (a) to (b)+(c) is more than about 0.16 to one it is necessary to add additional solubilizing substances (e), chosen from the group comprising (a) a nonionic surfactant selected from the group consisting of the following formulae:

$$R-X-(CH_2CH_2-O)_nH \quad (1)$$

where $n \times 44$ equals about 60 percent or more of the molecular weight of the surfactant molecule, and where X is O, S, or N, and R is a hydrocarbon radical with at least 10 carbon atoms; and (2) block copolymers of ethylene oxide and propylene oxide with a polymer molecular weight of at least 1000 present at a weight ratio of nonionic surfactant to amine oxide of from about 10 to 1 to about 1 to 10; (b) a phosphate ester of the general formula:

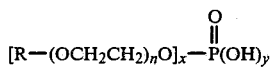

where x+y equals 3, R is $C_4$ to $C_{18}$ hydrocarbon, and n is such that $n \times 44$ is at least six times the molecular moiety weight of R, present at a weight ratio of phosphate ester to amine oxide of from about 1 to 10 to about 3 to 1, and (c) a water soluble alcohol solvent; said group substance (e) present at a concentration sufficient to render the composition transparent.

The surfactant amine oxides must be present at a concentration greater than their critical micelle concentration. The reaction of amine oxides with iodine in aqueous solution does not occur in the absence of amine oxide micelles.

Since much of the experimental evidence for the foregoing reactions came from studies of electronic spectra, an experiment of this nature is described herein.

ELECTRONIC SPECTRA

An iodophor was prepared by mixing 200 g of a 30 percent solution of tetradecyldimethylamine oxide with 446 ml of 4.93 percent phosphoric acid, and adding 3.0 g of crystalline iodine. The mixture was held at 70° C. for 30 minutes, and then stirred mechanically for one hour as it cooled. The pH of the solution was 3.0. The active iodine was 0.236 percent, determined by thiosulfate titration, and the triiodide ion was thus 0.354 percent since one triiodide ion consumes the same amount of the thiosulfate as does one $I_2$ molecule. (The added iodine was 0.448 percent, so there was 0.094 percent iodide ion in addition.)

The iodophor was diluted to 0.0244 percent amine oxide and 0.00096 percent triiodide ion. The electronic spectrum was obtained on a Cary Model 14 recording spectrophotometer from 500 nm to 200 nm.

Three absorption maxima appeared in this region, at 363 nm, 293 nm, and 225 nm. The first two are characteristic of triiodide ion in nonpolar solvents, where it is known to be an undissociated salt with its corresponding cation. The absorption is not at the wave lengths produced from $I_2/KI$ solutions where no association occurs between the $K^+$ ion and the triiodide ion. Therefore the triiodide ion is not free in solution and is associated with the protonated amine oxide cation. The third is characteristic of the iodide ion in water. The triiodide ion concentration as determined from an analysis of the solution's uv absorption was equal to that expected from the active iodine titration, if all the active iodine exists as triiodide. The sum of the concentration of iodide ion (in weight percent) and triiodide ion (in weight percent) determined from the intensity of the absorption was equal to the weight percent of iodine added. Since there was no detectable maximum at 450–460 nm (where molecular iodine in water absorbs), and furthermore all the added iodine could be accounted for as iodide and triiodide, it was shown that there is no molecular iodine present, and thus all of the active iodine is undissociated triiodide ion. This form of iodine has excellent biocidal properties, but reacts slowly with organic matter and does not vaporize, so that iodine in dilute solutions of these iodophors is extremely stable.

The same technique was used to show that, when iodophors of nonionic surfactants, iodophors of phosphate esters of nonionic surfactants, and iodophors of polyvinylpyrrolidone were diluted to 50 ppm active iodine or less, the iodine was mostly dissociated from the surfactant and existed as the molecular species $I_2$. Since molecular iodine reacts rapidly with organic matter, and is also lost through vaporization, the iodine in dilute solutions of these iodophors is unstable.

Compositions of the following examples for convenience are described in terms of the ingredients that were mixed to prepare them. It is understood that the amine oxides, iodine and acids react as described above to form the products (a) and (b) also described above. All percents are percents by weight.

EXAMPLE 1

LOW IODINE VAPOR PRESSURE

A formula containing:
2.0% phosphate ester of nonylphenol+30 moles of ethylene oxide
1.0% cetyldimethylamine oxide
3.0% iodine complex of nonylphenol+8-9 moles of ethylene oxide, containing 20% available iodine
q. s. water and a second formula containing:
2.0% phosphate ester of nonylphenol+30 moles of ethylene oxide
2.0% iodine complex of nonylphenol+8-9 moles of ethylene oxide, containing 20% available iodine
q. s. water were placed in open containers and a white porcelain tile was placed over each container. Iodine sublimation that occurred was photographed. No apparent sublimation occurred over the formula containing cetyldimethylamine oxide indicating that the iodine vapor pressure is very low, whereas the white tile over the second formula was stained brown from iodine vapor.

EXAMPLE 2

BIOCIDAL ACTIVITY

An amine oxide iodophor was prepared by mixing 66.7 g of 30 percent myristyldimethylamine oxide in water with 149 ml of 0.5N. $H_3PO_4$ and then adding 1.0 g of iodine. The mixture was heated at 70° C. for ½ hour, and agitated as it cooled to dissolve the iodine. A portion was diluted 1 to 10. It contained 0.90 percent amine oxide and 0.0191 percent iodine by thiosulfate titration. The pH was 3.0.

A typical nonionic iodophor was prepared by mixing 0.0967 g of Biopal VRO-20 (20 percent active iodine in nonylphenol condensed with 8–9 moles of ethylene oxide), 0.91 g of the ethoxylated nonylphenol Igepal CO-710, 7.7 ml of 0.468M $H_3PO_4$, 7.1 ml of 0.502N NaOH, and 80.8 g of water. This mixture contained 1.02 percent nonionic surfactant and 0.0188 percent iodine by thiosulfate titration. The pH was 3.0.

The biocidal activity of these two iodophors was determined by the A. O. A. C. use dilution procedure. The results appear in Table 3.

TABLE 3

|  | Dilution | ppm Surfactant | ppm Iodine | P. aeruginosa | S. aureus | S. choleraesu |
|---|---|---|---|---|---|---|
| myristyl-dimethyl-amine oxide iodophor | 1:3.80 | 2340 | 50 | — | — | — |
|  | 1:7.60 | 1170 | 25 | — | — | — |
|  | 1:19.0 | 468 | 10 | — | + | — |
|  | 1:38.0 | 234 | 5 | — | + | — |
| ethoxylated nonylphenol iodophor | 1:3.80 | 2600 | 50 | — | + | — |
|  | 1:7.60 | 1300 | 25 | + | + | — |
|  | 1:19.0 | 520 | 10 | + | + | — |
|  | 1:38.0 | 260 | 5 | + | + | — |

Compositions suitable for liquid products for cleansing and degerming skin for use as surgical scrubs, health care personnel hand washes, hand washes for food handlers and the like are those in which the concentration of (a) is from about 0.05% to 2.5%, the concentration of (a)+(b)+(c) is from about 3% to 15%, the alkyl or acyl group in $R_1$ contains about 12 to 16 carbon atoms, and the pH is from about 2.4 to 4.3. Optionally they may contain the additional materials of (e). Preferred is the phosphate ester of nonylphenol condensed with 30 to 50 moles of ethylene oxide. Other adjuvants which may be added are (1) from about 0.1% to 2% polyethylene oxide or hydroxyethyl cellulose of molecular weight greater than 100,000. This gives the composition desired viscosity and lubricity.

(2) from about 0.5% to 5% 2-pyrrolidone-5-carboxylic acid. This is a natural humectant and improves the cosmetic appeal of the compositions.

(3) acid and oxidation stable opacifiers and dyes, present at concentrations that give the compositions appealing appearance, preferrably from about 0.2 to 5% opacifying agent, and from about 0.002 to about 0.02% dye;

(4) quaternary ammonium salts containing at least one alkyl group having between 10 and 18 carbon atoms, the weight ratio of the quaternary ammonium salt to (a)+(b)+(c) being from about 0.1 to 1 to 1 to 1. The quaternary ammonium salts give the scrubs enhanced emolliency and lather. Examples 3 through 12 show such compositions.

EXAMPLE 3

| Ingredient | percent by weight |
|---|---|
| Dodecyldimethylamine oxide | 5.0 |
| Iodine | 0.50 |
| Phosphoric acid | 1.50 |
| Water | balance |

EXAMPLE 4

| Tetradecyldimethylamine oxide | 5.0 |
|---|---|
| Iodine | 0.50 |
| Phosphoric acid | 1.50 |
| Water | balance |

The compositions of Examples 3 and 4 are prepared by mixing 16.7 parts (by weight) of a 30 percent aqueous solution of the amine oxide with 1.76 parts of 85 percent phosphoric acid, and then adding 0.5 parts of crystalline iodine. The mixture is stirred at 60° C. for one hour and then diluted with 81 parts of water.

EXAMPLE 5

| Tetradecyldimethylamine oxide | 10.0 |
|---|---|
| Phosphate ester of nonylphenol + 50 moles of ethylene oxide | 16.7 |
| Iodine | 0.43 |
| Water | balance |

The phosphate ester in this formula improves the viscosity and cosmetic feel of the composition. Since the phosphate ester is also a suitable acid, no other acid is necessary.

EXAMPLE 6

| n-alkyl ($C_{14}$, 50%; $C_{12}$, 40%; $C_{16}$, 10%) dimethylamine oxide | 6.8 |
|---|---|
| Phosphate ester of nonylphenol + 50 moles of ethylene oxide | 11.2 |
| Iodine | 1.69 |
| Water | balance |

Since the molar ratio of amine oxide to triiodide ion in this composition is 5.6 to 1, the phosphate ester is necessary to solubilize the amine oxide-triiodide ion pair.

EXAMPLE 7

| n-alkyl ($C_{14}$, 50%; $C_{12}$, 40%; $C_{16}$, 10%) dimethylamine oxide | 6.0 |
|---|---|
| Ethoxylated cetyl and stearyl alcohols, 65% ethylene oxide | 7.0 |
| Iodine | 0.30 |
| Phosphoric acid | 2.0 |
| Water | balance |

This composition passed the A. O. A. C. "Chlorine Equivalency Test" at 0.06 percent active iodine.

EXAMPLE 8

| n-alkyl ($C_{12}$, 52.4%; $C_{14}$, 39.3%; $C_{16}$, 8.3%) dimethylamine oxide | 10.5 |
|---|---|
| Nonylphenol + 10 moles of ethylene oxide | 2.5 |
| Iodine | 2.0 |

| | |
|---|---|
| Phosphoric acid | 2.55 |
| Water | balance |

Since the molar ratio of amine oxide to triiodide ion in this composition is 5.0 to 1, the nonionic is necessary to solubilize the amine oxide-triiodide ion pair. This composition with 25 percent glycerin replacing part of the water remains high lathering.

EXAMPLE 9

| | |
|---|---|
| n-alkyl ($C_{14}$, 50%; $C_{12}$, 40%; $C_{16}$, 10%) dimethylamine oxide | 7.5 |
| Polyethylene oxide, m.w. 250,000 | 0.89 |
| Iodine | 0.58 |
| Phosphoric acid | 2.67 |
| Water | balance |

The polyethylene oxide gives the composition desired viscosity and a more luxurious feel.

EXAMPLE 10

| | |
|---|---|
| Myristyldimethylamine oxide | 6.0 |
| Phosphate ester of nonylphenol + 50 moles of ethylene oxide | 10.0 |
| Iodine | 0.5 |
| 2-pyrrolidone-5-carboxylic acid | 3.0 |

The 2-pyrrolidone-5-carboxylic acid improves the cosmetic appeal of this composition by improving the emolliency of the lather.

EXAMPLE 11

| | |
|---|---|
| Myristyldimethylamine oxide | 5.0 |
| Phosphate ester of nonylphenol + 50 moles of ethylene oxide | 16.7 |
| Iodine | 0.47 |
| Polystyrene opacifier | 4.0 |
| Water | balance |

This composition has a pleasing opaque light yellow appearance. It contained a biocidal level of iodine after standing three years at room temperature. The addition of 0.008 percent Neptune blue dye changed the color of the formulation to a light green and did not affect the stability of the iodine.

EXAMPLE 12

Compositions A through F contain amine oxide iodophors and quaternary ammonium salts. Table 4 describes their appearance, and rates their lather and emolliency on a scale of 1-excellent, 2-good, 3-fair, and 4-poor.

| Composition A | |
|---|---|
| n-alkyl ($C_{14}$, 50%; $C_{12}$, 40%; $C_{16}$, 10%) 5 dimethylamine oxide | 6.0 |
| Dicocodimethylammonium chloride | 5.0 |
| Iodine | 0.5 |
| Malic acid | 2.0 |
| Isopropanol | 1.7 |
| Water | balance |
| Composition B | |
| Cocodimethylamine oxide | 6.0 |
| Stearyl bis 2-hydroxyethylmethyl-ammonium chloride | 3.0 |
| Iodine | 0.50 |
| Malic acid | 2.0 |
| Water | balance |
| Composition C | |
| n-alkyl ($C_{14}$, 50%; $C_{12}$, 40%; $C_{16}$, 10%) dimethylamine oxide | 7.5 |
| N—stearoylcolaminoformylmethylpyridinium chloride | 2.0 |
| Iodine | 0.6 |
| Malic acid | 2.5 |
| Water | balance |
| Composition D | |
| Cetyldimethylamine oxide | 6.0 |
| Didecyldimethylammonium chloride | 3.0 |
| Iodine | 0.5 |
| Phosphoric acid | 2.0 |
| Isopropanol | 10.2 |
| Water | balance |
| Composition E | |
| Cetyldimethylamine oxide | 6.0 |
| Cetyltrimethylammonium chloride | 6.0 |
| Iodine | 0.50 |
| Malic Acid | 2.0 |
| Isopropanol | 9.0 |
| Water | balance |
| Composition F | |
| n-alkyl ($C_{12}$, 69%; $C_{14}$, 25%; $C_{16}$, 6%) dimethylamine oxide | 3.0 |
| Cetyldimethylamine oxide | 3.0 |
| Distearyldimethylammonium chloride | 5.0 |
| Iodine | 0.50 |
| Phosphoric acid | 2.0 |
| Isopropanol | 9.5 |
| Water | balance |

TABLE 4

| Composition | Appearance | Freeze-thaw stability | Lather | Emolliency |
|---|---|---|---|---|
| A | clear, good viscosity | stable | 1 | 2 |
| B | clear, very thin | stable | 1 | 1 |
| C | clear, good viscosity | stable | 1 | 1 |
| D | clear, thin | stable | 1 | 2 |
| E | clear, thin | stable | 1 | 1 |
| F | thick suspension | not stable | 2 | 1 |

Compositions suitable for iodine containing bars are those in which the concentration of (a) is from about 0.05% to 5%, the concentration of (a)+(b)+(c) is from about 3% to 30%, and which contain from about 50% to 90% of a nonionic surfactant with a melting point above 45° C.

EXAMPLE 13

| | |
|---|---|
| Dodecyldimethylamine oxide | 20.0 |
| Block copolymer of propylene oxide and ethylene oxide, m.w. 12,500, 70% ethylene oxide | 60.0 |
| Iodine | 2.0 |
| Phosphoric acid | 8.3 |
| Water | balance |

This composition is a bar with high, luxurious lather. It is suitably hard and non-hygroscopic. It is clear and the dark red color of the triiodide ion. The iodine was stable for over one year exposed to the air, and did not disappear as the bar was consumed in washing the hands.

EXAMPLE 14

Compositions of Examples 5 and 7 were prepared without amine oxide, i.e., iodophors of the phosphate ester of nonylphenol+50 moles of ethylene oxide, and of cetyl and stearyl alcohol ethoxylates containing 65 percent ethylene oxide were prepared at pH 2.5. The lather and emolliency were evaluated as per Example 12. The results are shown in Table 5.

TABLE 5

|  | Lather | Emolliency |
|---|---|---|
| Composition of Example 5 | 1 | 2 |
| Composition of Example 5 without amine oxide | 4 | 2 |
| Composition of Example 7 | 1 | 1 |
| Composition of Example 7 without amine oxide | 4 | 2 |

EXAMPLE 15

Compositions were prepared according to the procedure of Examples 3 and 4, having the composition:
5.0% amine oxide
0.5% iodine
1.5% phosphoric acid Table 6 lists the amine oxides incorporated into the composition, and the active iodine remaining after the compositions had stood for one year at room temperature. (If all of the added iodine is present as triiodide ion the active iodine is 0.333%)

TABLE 6

|  | Amine oxide | Percent active iodine after one year at room temperature |
|---|---|---|
| A | decyldimethylamine oxide | 0.268 |
| B | decyl bis(2-hydroxyethyl)amine oxide | 0.186 |
| C | dodecyldimethylamine oxide | 0.226 |
| D | cocodimethylamine oxide | 0.051 |
| E | coco bis(2-hydroxyethyl)amine oxide | 0 |
| F | stearyldimethylamine oxide | 0.221 |
| G | tallow bis(2-hydroxyethyl)amine oxide | 0 |

It is noted that the iodine is less stable if (1) the amine oxides are derived from natural products (D, E, and G), and (2) the methyl groups of the amine oxide are replaced by 2-hydroxyethyl groups (B, E, and G). Emolliency can be improved by incorporating an iodine stable emollient. Synthetic compounds and mineral oils are preferred to those derived from natural products because the synthetic compounds and mineral oils have better stabilit in the presence of iodine. These emollients can be incorporated at levels from 2% to 50% depending on the effects desired.

EXAMPLE 16

| Ingredient | Percent by weight |
|---|---|
| Composition A | |
| n-alkyl (C$_{14}$, 50%; C$_{12}$, 40%; C$_{16}$, 10%) dimethylamine oxide | 10.0 |
| polymerized, hydrogenated decene-1 | 20.0 |
| 2-pyrrolidone-5-carboxylic acid | 3.0 |
| phosphoric acid | 2.0 |
| iodine | 0.3 |
| water | balance |
| Composition B | |
| stearyldimethylamine oxide | 4.0 |
| refined mineral oil | 35.0 |
| citric acid | 1.5 |
| iodine | 0.5 |
| water | balance |

These compositions are emulsions. Composition A lathers and is suitable for use as a lotion cleanser. Formula B is an antiseptic emollient cream. The addition of 5 percent of a C$_{16}$ to C$_{18}$ alcohol ethoxylated with 65 percent ethylene oxide improved the emulsion stability of Composition A.

EXAMPLE 17

Amine oxide iodophors can be prepared using other iodophors as the source of iodine. Thus a composition of this invention suitable for surgical scrub was prepared using PVP-I as the iodine source (composition A).

The PVP-I was prepared according to Siggia, U.S. Pat. No. 2,900,305. The iodine stability was compared to that of a typical surgical scrub prepared from PVP-I and the ammonium salt of the ether sulfate of nonylphenol condensed with 4 moles of ethylene oxide as the foaming agent (composition B).

| Composition A | |
|---|---|
| myristyldimethylamine oxide | 6.0 |
| PVP-I | 4.67 |
| phosphoric acid | 2.0 |
| hydroxyethyl cellulose | 0.4 |
| water | balance |
| Composition B | |
| ethyloxylated nonylphenol ether sulfate | 15 |
| PVP-I | 7.5 |
| trisodium phosphate | 0.29 |
| trisodium citrate | 0.12 |
| hydroxyethyl cellulose | 0.4 |
| water | balance |

The iodine remaining was titrated after storage at room temperature with the following results.

| | % iodine remaining | |
|---|---|---|
| Number of days | Composition A | Composition B |
| 0 | 0.436 | 0.837 |
| 148 | 0.433 | 0.783 |
| 236 | 0.429 | 0.748 |

The amine oxide composition A maintained 98% of its original iodine level after 236 days, whereas the PVP-I composition B had dropped to 89% of the origin level. The United States Pharmaecopia requires that iodine compositions contain at least 85% of the iodine level stated on the label. Using this criterion, the amine oxide composition A could be projected to have a shelf life of about 6 years, whereas the shelf life of PVP-I composition B is about 11 months. Polyvinyl pyrrolidone itself as well as PVP can be added to the compositions of this invention at concentration from about 1% to about 20% to form products which dry to cohesive films when applied to the skin.

EXAMPLE 18

A composition suitable for softening and degerming fabric was prepared from a 1:1 mixture of (a) an amine oxide-triiodide complex of equal portions of lauryl-, myristyl-, cetyl-, and stearyldimethylamine oxides in which the ratio of amine oxide to triiodide was 10 to 1, and (b) dihydrogenated tallow dimethyl ammonium chloride according to the teachings of U.S. Pat. No. 3,959,157 (incorporated herein by reference). The composition did not stain fabric, had good detergency, left the cloth with a soft hand and remained biocidal throughout the wash by which process the bacteria count on the fabric was greatly reduced.

EXAMPLE 19

| Ingredient | Percent by weight |
| --- | --- |
| n-alkyl ($C_{16}$, 55%; $C_{14}$, 25%, $C_{12}$, 20%) dimethylamine oxide | 25.0 |
| iodine | 5.0 |
| citric acid | 30.0 |
| water | balance |

This composition is a concentrate suitable for dilution to about 25 ppm active iodine to be used as a germicidal mouthwash. Compositions suitable for hard surface cleaners are those in which the concentration of (a) is from about 0.2% to 15%, the concentration of (a)+(b)=(c) is from about 0.5% to 40%, and the pH is 0.2 to 4.3.

EXAMPLE 20

| | |
| --- | --- |
| n-alkyl ($C_{16}$, 55%; $C_{14}$, 25%; $C_{12}$, 20%) dimethylamine oxide | 5.0 |
| iodine | 0.75 |
| phosphoric acid | 5.0 |
| water | balance |

This composition is a hard surface detergent suitable for 1/64 dilution possessing excellent detergency. It is also suitable for use in an automatic dispensing toilet bowl sanitizer. It possesses long lasting biocidal activity at high dilution and in the presence of organic matter, as shown by Example 21.

EXAMPLE 21

To demonstrate the improved iodine stability and biocidal activity of amine oxide iodophors compared to nonionic iodophors, PVP-iodine, and iodine with no complexing agent against *E. coli* and *S. aureus*, the following procedure was used.

200 mg of dehydrated nutrient broth was added to 1 l of distilled water at room temperature. An amount of the iodophor equivalent to 5 ppm active iodine in the dilution was added, and immediately 1 ml of a broth culture of the bacteria was added, equivalent to a count at the 1 l dilution of 100,000 to 200,000 per ml for *E. coli*, and 1,000 to 4,000 per ml for *S. aureus*. The iodophor dilutions were stirred continuously on a magnetic stirrer. At 30 seconds, 5 minutes, and 50 minutes after the bacteria were added 1 ml samples were taken and diluted immediately in 9 ml of 0.1 percent sodium thiosulfate. Surviving organisms were counted by standard millipore filter techniques. One hour after the first addition of bacteria the same bacteria count was introduced again by adding 1 ml of a broth culture of the bacteria, and surviving organisms counted at 30 seconds, 5 minutes and 50 minutes as before. The procedure was repeated at 2 hours, 4 hours, and 24 hours, except that the experiments were stopped when the iodine was completely gone.

The amine oxide iodophor of Example 20 showed 100 percent kill in 50 minutes with both bacteria when the iodophor dilution was 24 hours old. An iodophor of nonylphenol+8–9 moles of ethylene oxide, an iodophor of a block copolymer of propylene oxide and ethylene oxide, PVP-iodine, and iodine with no complexing agent showed no biocidal activity after the dilutions had stood for 1 hour.

EXAMPLE 22

| Ingredient | Percent by weight |
| --- | --- |
| Composition A | |
| n-alkyl ($C_{12}$, 69%; $C_{14}$, 25%; $C_{16}$, 5%) dimethylamine oxide | 10.0 |
| iodine | 0.80 |
| hydrochloric acid | 3.0 |
| water | balance |
| Composition B | |
| n-alkyl ($C_{12}$, 69%; $C_{14}$, 25%; $C_{16}$, 5%) dimethylamine oxide | 10.0 |
| iodine | 0.25 |
| hydrochloric acid | 3.0 |
| water | balance |
| Composition C | |
| n-alkyl ($C_{12}$, 69%; $C_{14}$, 25%, $C_{16}$, 5%) dimethylamine oxide | 5.0 |
| iodine | 0.40 |
| hydrochloric acid | 1.5 |
| water | balance |

Compositions A, B, and C are suitable for use as germicidal hard surface cleaners. After standing 9 months at room temperature, all of the iodine that had been added could be titrated with sodium thiosulfate, due to the formation of the $I_2Cl^-$ ion rather than the $I_3^-$ ion. The addition of 0.66 percent hydrogen peroxide to Composition A rendered it a light lemon yellow color which is the color of the $I_2Cl^-$ ion in the absence of the triiodide ion. Because the compositions of this invention have no iodine vapor pressure in dilute solutions products suitable for douches, mouthwashes and the like can be marketed in a prediluted form, eliminating the need for the consumer to dilute the product. Suitable compositions contain from about 0.005% to 0.2% (a), and from about 0.01% to 1% (a)+(b)+(c), the pH being from about 2.4 to 4.3.

EXAMPLE 23

To demonstrate iodine stability and low iodine vapor pressure in very dilute solutions, the following formulations suitable for ready-to-use douches were prepared.

| Ingredient | Percent by weight |
| --- | --- |
| Composition A | |
| Myristyl-cetyl dimethyl amine oxide | 0.19 |
| Phosphoric acid | 0.14 |
| Iodine | 0.038 |
| Water | balance |
| pH = 3.0 | |
| Composition B | |
| Myristyl-cetyl dimethyl amine oxide | 0.19 |
| Phosphoric acid | 0.14 |
| PVP-I containing 11.3% active iodine | 0.22 |
| Water | balance |
| pH = 3.0 | |
| Composition C | |
| Myristyl-cetyl dimethyl amine oxide | 0.19 |
| Phosphoric acid | 0.41 |
| PVP-I containing 11.3% active iodine | 0.22 |
| Water | balance |
| pH = 2.5 | |
| Composition D | |

-continued

| Ingredient | Percent by weight |
| --- | --- |
| Myristyl-cetyl dimethyl amine oxide | 0.12 |
| Phosphoric acid | 0.15 |
| PVP-I containing 11.3% active iodine | 0.22 |
| Nonylphenol + 9 EO | 0.085 |
| Water | balance |
| pH = 3.0 | |
| Composition E | |
| PVP-I containing 11.3% active iodine | 0.23 |
| Phosphoric acid | 0.03 |
| Water | balance |
| pH = 3.0 | |

All compositions contained approxiately 250 ppm active iodine stability. Portions were stored at 28°, 34°, and 50° C., and titrated for active iodine periodically for five weeks. This data was used to determine first order rate constants for the disappearance of titratable iodine over this period. The results are shown in the following table. The rates are compared to the rate for the PVP-I solution (E) at 28° C., which is arbitrarily 1.00.

| Composition | Relative rate of disappearance of $I_2$ | | |
| --- | --- | --- | --- |
| | 28° | 34° | 50° |
| A | 0.65 | 0.63 | 3.50 |
| B | 0.47 | 0.36 | 3.14 |
| C | 0.07 | 0.71 | 0.50 |
| D | 0.75 | 0.46 | 3.37 |
| E | 1.00 | 3.25 | 9.78 |

Iodine vapor was readily visible above the PVP-I solution (E). No iodine color or odor was detectable in any of the other solutions.

EXAMPLE 24

| Ingredient | Percent by Weight |
| --- | --- |
| Lauryldimethylamine oxide | 2.5 |
| Myristyl-cetyldimethylamine oxide | 5.0 |
| Phosphoric acid | 2.67 |
| Iodine | 0.58 |
| pH = 2.8 | |

This formulation was allowed to stand at room temperature and titrated periodically. The results are shown in the table.

| Age (days) | Percent Active Iodine |
| --- | --- |
| 0 | 0.264 |
| 26 | 0.259 |
| 38 | 0.260 |
| 56 | 0.266 |
| 308 | 0.262 |
| 1419 | 0.268 |

This shown that the iodine in these iodophors reaches a stable level and does not change with time.

Other modifications of this invention will be apparent to those skilled in the art.

We claim:

1. A stable aqueous biocidal solution comprising
(a) an undissociated and by itself insoluble protonated amine oxide-triiodide salt of the structure

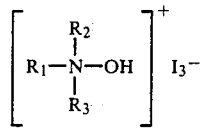

(b) a protonated amine oxide salt of the structure

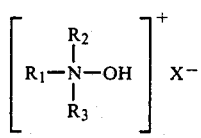

(c) an amine oxide of the structure

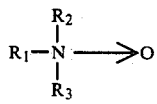

(d) a water soluble acid of the structure HY
(e) one or more substances chosen from the group consisting of
  (1) surface active phosphate esters
  (2) nonionic surfactants
  (3) water soluble solvent alcohols wherein $R_1$ is alkyl containing about 10 to 18 carbon atoms and no unsaturation; $R_2$ and $R_3$ are methyl; Y is a radical selected from the group consisting of phosphate and phosphate esters, chloride, bromide, lactate, citrate, malate, glycolate, formate, oxalate, tartrate, and sulfate; and X is a radical selected from the group consisting of iodide and Y; the molar ratio of (a) to (b)+(c) being less than about 0.5 to 1, the molar ratio of (b) to (c) being at least about 2 to 1; (d) being present at a level sufficient to effect a pH of about 4.3 or lower; and (b)+(c) or said group substance (e), or (b)+(c) and said group substance (e) taken together being present in an amount at least sufficient to effect a transparent solution; said solution containing no molecular iodine as determined spectrophotometrically; said biocidal solution resulting from mixing a water solution of from about 2 to 67 molar equivalents of one or more amine oxides of structure (c) with one molar equivalent of iodine, acid (d) in sufficient quantity to lower the pH to about 4.3 or lower, and sufficient said group substance (e) to effect a transparent solution.

2. The composition of claim 1 wherein the concentration of (a) is from about 0.2% to 15%, the concentration of (a)+(b)+(c) is from about 0.5% to 40%, and the pH is from about 0.2 to 4.3.

3. The composition of claim 1 wherein the concentration of (a) is from about 0.005% to 0.2%, and the concentration of (a)+(b)+(c) is from about 0.01% to 1%, and the pH is from about 2.4 1 to 4.

4. The solution of claim 1 wherein said phosphate ester has the structure

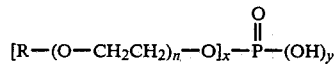

wherein x+y equals 3, R is $C_4$ to $C_{18}$ hydrocarbon, and n is such that $n \times 44$ is at least six times the molecular moiety weight of R, present at about 1 percent to about 25 percent of the composition, but in no case in excess of a weight ratio of phosphate ester to amine oxide of about 3 to 1.

5. The solution of claim 1 wherein said nonionic surfactant has the structure $$R\text{-}X\text{-}(CH_2CH_2\text{-}O)_nH$$

wherein $n \times 44$ equals about 60 percent or more of the molecular weight of said nonionic surfactant and where X is O, S, or N, and R is a hydrocarbon radical with at least 10 carbon atoms, the weight ratio of the amine oxide to the nonionic surfactant is between about 10 to 1 and 1 to 10.

6. The solution of claim 1 wherein said nonionic surfactant is a block copolymer of propylene oxide and ethylene oxide with a molecular weight of at least about 1000.

7. The solution of claim 1 wherein the concentration of (a) is from about 0.05% to 5%, the concentration of (a)+(b)+(c) is from about 3% to 30%, in admixture with from about 50% to 90% of a nonionic surfactant with a melting point above about 45° C.

8. The solution of claim 1 in admixture with from about 0.2% to 5% of an acid and oxidation stable opacifying agent.

9. The solution of claim 1 in admixture with from about 0.002% to 0.2% of an acid and oxidation stable dye.

10. The solution of claim 1 containing from about 1 to 20 percent by weight of polyvinylpyrrolidone.

11. The solution of claim 1 in admixture with from about 2% to 50% mineral oil.

12. The solution of claim 1 in admixture with one or more quaternary ammonium salts containing at least one alkyl group having between 10 and 18 carbon atoms, the weight ratio of the quaternary ammonium salt to (a)+(b)+(c) being from about 0.1 to 1 to 1 to 1.

13. The solution of claim 12 in which the quaternary ammonium salt is selected from the group consisting of
   (a) N-stearoylcolaminoformylmethylpyridinium halide and N-palmitoylocolaminoformylmethylpyridinium halide, and mixtures thereof
   (b) di-higher alkyl dimethyl ammonium halides, said higher alkyls having 12 to 18 carbon atoms
   (c) stearyl bis 2-hydroxyethyl methyl ammonium halide, and
   (d) higher alkyl trimethyl ammonium halides, said higher alkyls having 16 to 18 carbon atoms.

14. The composition of claim 1 wherein the concentration of (a) is from about 0.05% to 2.5%, the concentration of (a)+(b)+(c) is from about 3% to 15%, the alkyl or acyl group in $R_1$ contains about 12 to 16 carbon atoms, and the pH is from about 2.4 to 4.3.

15. The solution of claim 14 in admixture with from about 0.1% to 2% polyethylene oxide or hydroxyethyl cellulose of molecular weight greater than about 100,000.

16. The solution of claim 14 in admixture with from about 0.5% to 5% 2-pyrrolidone-5-carboxylic acid.

17. The solution of claim 14 in which $R_1$ is a straight-chain alkyl containing from about 12 to 16 carbon atoms, or mixtures thereof, and $R_2$ and $R_3$ are methyl.

18. A stable aqueous biocidal solution comprising
   (a) an undissociated and by itself insoluble protonated amine oxide-trihalide salt of the structure

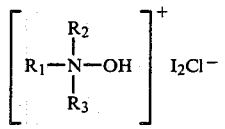

(b) a protonated amine oxide salt of the structure

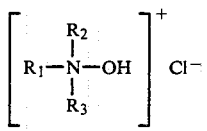

(c) hydrochloric acid wherein $R_1$ is alkyl containing about 10 to 18 carbon atoms and no unsaturation; $R_2$ and $R_3$ are methyl; the molar ratio of (a) to (b) being between about 0.2 to 1 and 0.01 to 1; and the molar ratio of (c) to (a)+(b) being at least about 1 to 1; said solution containing no molecular iodine as determined spectrophotometrically; said biocidal solution resulting from mixing a water solution of from about 6 to about 100 molar equivalents of one or more amine oxides of the structure

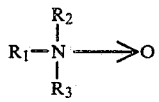

wherein $R_1$, $R_2$, and $R_3$ are described above; with one molar equivalent of iodine and at least one molar equivalent of hydrochloric acid (c) per molar equivalent of amine oxide.

* * * * *